United States Patent
Kitamura et al.

(10) Patent No.: US 9,989,549 B2
(45) Date of Patent: Jun. 5, 2018

(54) AUTOMATIC ANALYZER

(75) Inventors: Masakazu Kitamura, Tochigi-ken (JP); Tomohiro Sugimura, Tochigi-ken (JP); Takehiko Oonuma, Tochigi-ken (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days. days.

(21) Appl. No.: 13/104,051

(22) Filed: May 10, 2011

(65) Prior Publication Data

US 2011/0274584 A1    Nov. 10, 2011

(30) Foreign Application Priority Data

May 10, 2010    (JP) .................. 2010-108395

(51) Int. Cl.
G01N 35/10    (2006.01)

(52) U.S. Cl.
CPC ............... G01N 35/1004 (2013.01)

(58) Field of Classification Search
None
See application file for complete search history.

(56) References Cited

U.S. PATENT DOCUMENTS

| | | | | |
|---|---|---|---|---|
| 4,398,894 | A * | 8/1983 | Yamamoto | 436/517 |
| 6,422,248 | B1 * | 7/2002 | Furst et al. | 134/22.11 |
| 2009/0041622 | A1 * | 2/2009 | Maeda et al. | 422/63 |
| 2010/0051060 | A1 * | 3/2010 | Kuroda et al. | 134/22.11 |

FOREIGN PATENT DOCUMENTS

| | | |
|---|---|---|
| JP | 10-267939 | 10/1998 |
| JP | 2001-305148 | 10/2001 |
| JP | 2002-162403 | 6/2002 |
| JP | 2003-240787 | 8/2003 |
| JP | 2005-000775 | 1/2005 |

(Continued)

OTHER PUBLICATIONS

English translation of JP 2005-000775A (Japan) to Nippon Pulse Motor Co. LTD, Published Jan. 6, 2005.*

(Continued)

Primary Examiner — P. Kathryn Wright
(74) Attorney, Agent, or Firm — Oblon, McClelland, Maier & Neustadt, L.L.P.

(57) ABSTRACT

An automatic analyzer that dispenses a sample and a reagent in a reaction cuvette and measures the mixed solution, including a dispensing probe configured to suction the sample from the sample container and to discharge the sample into the reaction cuvette; a detecting unit configured to detect the sample in the sample container by the end part of the dispensing probe contacting the sample; and a washing unit configured to wash a wide range of the external surface containing a broad end part, rather than the end part of the dispensing probe, which keeps the suctioned sample in the sample container in a second downward suction position, rather than a first suction position detected by the detection unit, wherein the washing unit is configured to have a washing tube, wherein the dispensing probe enters into an upper part of the washing tube, and a pump that supplies the washing tube with cleaning liquid and makes the cleaning liquid flow up through the inside of the washing tube.

10 Claims, 10 Drawing Sheets

(56) References Cited

FOREIGN PATENT DOCUMENTS

| | | |
|---|---|---|
| JP | 2005-265808 | 9/2005 |
| JP | 2006-126016 | 5/2006 |
| JP | 2007-93220 A | 4/2007 |
| JP | 2008-281480 | 11/2008 |
| JP | 2009-222593 | 10/2009 |
| JP | 2010-048594 A | 3/2010 |
| JP | 2010-71765 * | 4/2010 |
| JP | 2010-085097 A | 4/2010 |

OTHER PUBLICATIONS

Office Action dated Nov. 4, 2014 in Japanese Patent Application No. 2011-104758 (with English language translation).

* cited by examiner

AUTOMATIC ANALYZER

CROSS-REFERENCE TO RELATED APPLICATIONS

This application is based upon and claims the benefit of priority from prior Japanese Patent Application No. P2010-108395, filed May 10, 2010, the entire contents of which are incorporated herein by reference.

BACKGROUND

1. Field

Embodiments disclosed herein relate to an automatic analyzer having a mechanism that washes the dispensing probe that dispenses a liquid.

2. Description of the Related Art

An automatic analyzer generates analytical data expressed with a concentration of a test item component in a sample, the activity of enzyme, etc. by measuring optically a change of a color tone and turbidity produced by the reaction of a mixed-liquid of samples, such as a suspected sample extracted from a sample for a biochemistry test item, an immunological test item, etc., with a reagent of each analysis item in a light measurement part of a spectrum photometer or a nephelometry meter.

With this automatic analyzer, an analysis item set up out of two or more analysis items for every suspected sample is analyzed. Further, a photometry unit measures the mixed-liquid of the suspected sample and the reagent suctioned in a reaction cuvette. A sample dispensing probe is washed by a washing tank for every end of the sample dispensing probe. Moreover, a reagent dispensing probe is washed by a washing tank for every end used for reagent dispensing.

In addition, there is a blood collection tube that accommodates the whole blood collected from a subject in the sample container used with the automatic analyzer.

The whole blood accommodated in this blood collection tube is divided into an upper layer sample containing serum or plasma and a lower layer sample containing a blood cell component, etc. Further, the upper layer sample is dispensed and the dispensed sample is analyzed regarding each analysis item. When the upper layer sample is suctioned, the end of the sample dispensing probe may attract a sample in the position where the end part, which has fallen several mm from the surface, and the upper layer sample adheres to the end outside side of the sample dispensing probe. The sample adhering to the sample dispensing probe pollutes the sample in the sample container that is dispensed in the next dispensing. As a method of solving this problem, a washing method that washes the end outside side of a sample dispensing probe has been proposed (for example, see Japanese Patent No. 4175916).

Recently, the lower layer sample in a blood collection tube is dispensed and, for example, an analysis item of glycohemoglobin, etc. is analyzed. In suction of this lower layer sample, for example, in order to pass the upper sample and to attract the lower layer sample that is tens of mm below a surface, the sample adheres to a wide range external surface containing the end part of the sample dispensing probe. When the reaction cuvette is made to flow out the sample obtained after the sample had adhered to this sample dispensing probe external surface, the sample adhered outside falls into the reaction cuvette, and there is a problem in which the dispensing accuracy of the lower layer sample is lower. Moreover, there is a problem that the next dispensed sample in the sample container is polluted by the sample that adheres to the outside of the sample dispensing probe.

If one tries to wash away the sample adhering to the wide range external surface of the sample dispensing probe by the method indicated by U.S. Pat. No. 4,175,916 in order to solve this problem, it is necessary to enlarge the path of the washing tube. Further, in order to prevent spilling of washing water, it is necessary to emit a lot of washing water with a strong pressure. Therefore, it is necessary to enlarge the washing tank to prevent the spilling of washing water.

By the way, a washing method that washes the external surface of a reagent dispensing probe is known (for example, see Japanese patent application publication No. 2002-162403). It is possible using this method to wash the sample dispensing probe. By the washing method indicated by Japanese patent application publication No. 2002-162403, the cleaning liquid spouts so that it will be applied and wash the sample dispensing probe.

However, due to the position where the cleaning liquid is applied, and because it is difficult to make the cleaning liquid cover the whole wide range external surface of the sample dispensing probe, the sample remains on the sample dispensing probe external surface, and there is a problem that the next dispensed sample in the sample container is polluted by the sample that adhered outside of the sample dispensing probe.

SUMMARY

Embodiments disclosed herein solve the problems described above, and an object of the disclosed embodiments is to provide an automatic analyzer that can wash the external surface in contact with the sample of the sample dispensing probe, without reducing the dispensing accuracy of the lower layer sample.

BRIEF DESCRIPTION OF THE DRAWINGS

Aspects of the disclosed embodiments will become apparent upon reading the following detailed description and upon reference to the accompanying drawings. The description and the associated drawings are provided to illustrate the disclosed embodiments and do not limit the scope of the disclosed embodiments.

DETAILED DESCRIPTION

Hereafter, embodiments of the automatic analyzer are explained with reference to FIGS. 1-10.

Figure 1:
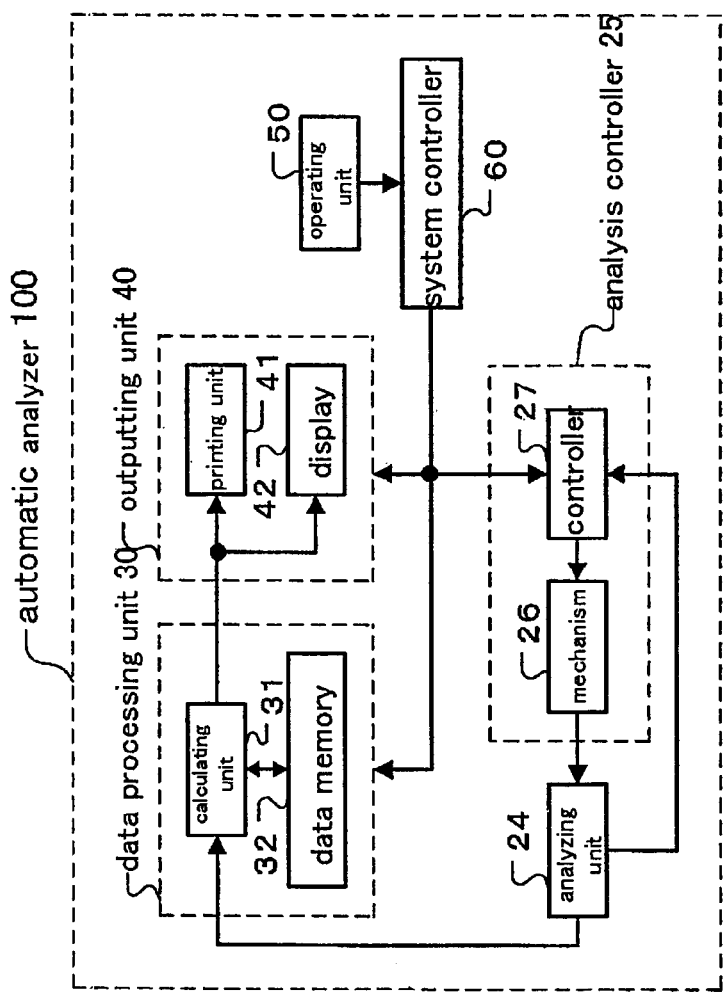
FIG. 1 is a block diagram showing the composition of the automatic analyzer in one embodiment.

FIG. 1 is a block diagram showing the composition of the automatic analyzer in one embodiment.

The automatic analyzer 100 includes an analyzing unit 24 that measures a mixed-solution comprising a sample, for example, a standard sample or a suspected sample and a reagent used in the analysis of each analysis item dispensed by the dispensing probe, and generates standard data and suspected data, and an analysis controller 25 that drives each unit of the analyzing unit 24 and controls a dispensing operation, measurement operation, washing operation, etc.

Moreover, the automatic analyzer 100 has a data processing unit 30 that processes standard data and suspected data that were generated in the analyzing unit 24 and generates calibration data and analytical data, an outputting unit 40 that prints or displays the calibration data and the analytical data, an operating unit 50 to input various command signals, and a system controller 60 that controls the analysis controller 25, the data processing unit 30, and the outputting unit 40.

Figure 2:
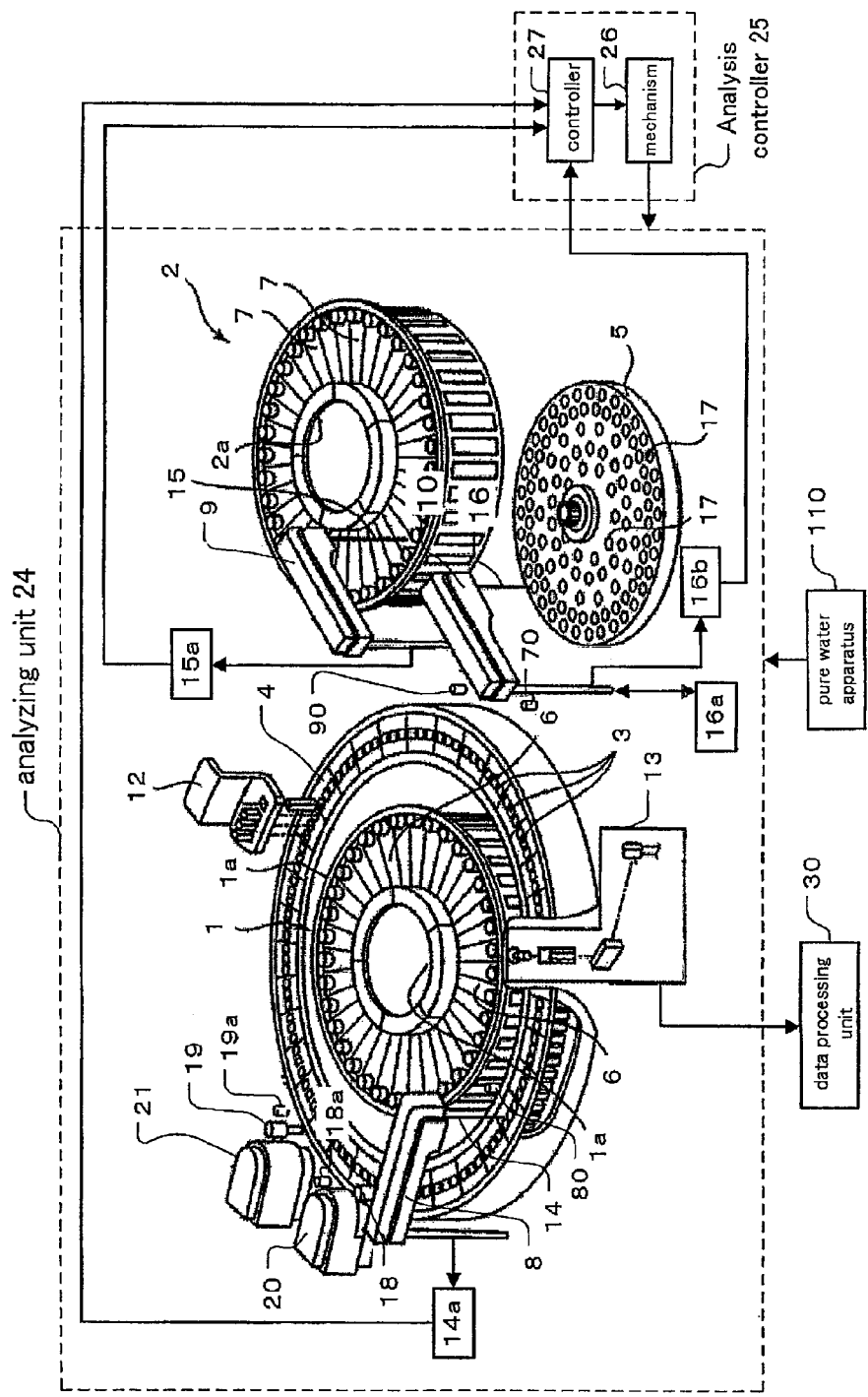
FIG. 2 is a perspective diagram showing the composition of the analyzing unit in one embodiment.

FIG. 2 is a perspective diagram showing the composition of the analyzing unit 24. The analyzing unit 24 includes a sample container 17 that accommodates each suspected sample, such as the standard sample, urine, whole blood, an up-and-down layer separation sample separated into up-and-down layers from whole blood, and the suspected sample that includes an upper layer sample, for example, the serum and plasma, a sample disc 5 that holds the sample container 17, a reagent container 6 that holds the first reagent of reagent system 1 and reagent system 2 that reacts with the component of the analysis item containing each sample such as the standard sample and the suspected sample, and a reagent storage 1 that stores the reagent container 6, a reagent rack 1a that holds the reagent container 6, which is configured to rotate, a reagent container 7 that accommodates the second reagent that is a pair of the first reagent of reagent system 2, a reagent storage 2 that that stores the reagent container 7, and a reagent rack 2a that holds the reagent container 7, which is configured to rotate, and a reaction disc 4 that holds a plurality of reaction cuvettes 3, which are configured to rotate.

Moreover, the analyzing unit 24 has a sample dispensing probe 16 that suctions each sample in the sample container 17 held in the sample disc 5 and discharges the sample into the reaction cuvette 3, a sample dispensing pump 16a that causes the sample dispensing probe 16 to suction and discharge the sample, and a sample dispensing arm 10 that holds the sample dispensing probe 16, and is able to rotate and move up and down. Further, the analyzing unit 24 has a washing unit 70 that washes the external surface that contacted the sample of the sample dispensing probe 16 using pure water manufactured with the pure water apparatus 110 as a cleaning liquid, and a sample detecting unit 16b, which detects the sample in the sample container 17 held in the sample disc 5 by contact with the sample and the end part of the sample dispensing probe 16.

Moreover, the analyzing unit 24 has a first reagent dispensing probe 14 that suctions the first reagent in the reagent container 6 held in reagent rack 1a and discharges the first reagent into the reaction cuvette 3 in which the sample is discharged, a first reagent dispensing arm 8 that holds the first reagent dispensing probe 14, which is configured to rotate and to move up and down, a washing unit 80 that washes the external surface of the first reagent dispensing probe 14 that contacted the first reagent, and a first reagent detecting unit 14a, which detects the first reagent in the reagent container 6 by contact with the end part of the first reagent dispensing probe 14.

Moreover, the analyzing unit 24 has a first stirring unit 18 that stirs the mixed liquid of the sample and the first reagent, and a first stirring arm 20 that holds the first stirring unit 18, which is configured to rotate and move up and down, and a washing tank 18a that washes the first stirring unit 18 for every churning end of the mixed liquid.

Moreover, the analyzing unit 24 has a second reagent dispensing probe 15 that suctions the second reagent in the reagent container 7 held in reagent rack 2a and discharges the second reagent into the reaction cuvette 3 in which the first reagent is discharged, a second reagent dispensing arm 9 that holds the second reagent dispensing probe 15, which is configured to rotate and to move up and down, a washing unit 90 that washes the external surface of the second reagent dispensing probe 15 that contacted the second reagent, and a second reagent detecting unit 15a that detects the second reagent in the reagent container 7 by contact with the end part of the second reagent dispensing probe 15.

Moreover, the analyzing unit 24 has a second stirring unit 19 that stirs the mixed liquid of the sample, the first reagent, and the second reagent, a second stirring arm 21 that holds the second stirring unit 19, which is configured to rotate and move up and down, a washing tank 19a that washes the second stirring unit 19 for every churning end of the mixed liquid, a photometry unit 13 that irradiates light into the mixed liquid in the reaction cuvette 3 and measures properties of the mixed liquid optically, and a reaction cuvette washing unit 12 that washes inside of the reaction cuvette 3 after the mixed liquid measurement is finished.

The photometry unit 13 irradiates light and detects the light that penetrates the mixed liquid containing the standard sample and each suspected sample in the reaction cuvette 3, which carries out a rotation movement and crosses the light path for every wavelength of an analysis item.

Further, based on the detected signal, the photometry unit 13 generates, for example, the standard data and the suspected data, which are expressed by absorbance data, and outputs the standard data and the suspected data to the data processing unit 30.

The analysis controller 25 is equipped with a mechanism part 26, which has a mechanism in which each unit of the analyzing unit 24 is driven, and a controller 27, which controls each mechanism of the mechanism part 26 and operates each unit of the analyzing unit 24.

The mechanism part 26 is equipped with a mechanism in which the sample disc 5, the reagent rack 1a, the reagent rack 2a, and the reaction disc 4 are rotated, respectively.

Moreover, the mechanism part 26 includes a mechanism in which the sample dispensing arm 10, the first reagent dispensing probe 8, the second reagent dispensing probe 9, the first stirring arm 20, and the second stirring arm 21 are rotated and moved up and down, respectively.

Moreover, the mechanism part 26 includes a mechanism that carries out up and down movement of the reaction cuvette washing unit 12. Moreover, the mechanism part 26 includes a mechanism that operates the sample dispensing pump 16a to suction and discharge, and operates the washing units 70, 80, and 90.

The controller 27 is equipped with a control circuit that controls each mechanism of the mechanism part 26 and operates each unit of the sample disc 5 of the analyzing unit 24, the reagent rack 1a, the reagent rack 2a, the reaction disc 4, the sample dispensing arm 10, the first reagent dispensing probe 8, the second reagent dispensing probe 9, the first stirring arm 20, the second stirring arm 21, the reaction cuvette washing unit 12, the sample dispensing pump 16a, and the washing units 70, 80, and 90.

Further, the controller 27 operates the rotating mechanism to rotate the sample dispensing arm 10 to cause the sample dispensing probe 16 to move to the height of the top dead point and to stop in each upper top position on the sample disc 5 and on the reaction disc 4, and in the first and second upper positions near the upper end of the washing unit 70.

Moreover, the controller 27 supplies a drive pulse to an up-and-down mechanism to move the sample dispensing arm 10 and to cause the sample dispensing probe 16 to move down from an upper stop position.

After stopping the sample dispensing probe 16 in the upper stop position of the sample disc 5, the controller 27 causes the sample dispensing probe 16 to move downward and to stop in each suctioning position of the first suction position, where the sample in the sample container 17 held at the sample disc 5 is detected by the sample detecting unit 16b, and the second suctioning position located below the first suctioning position by a predetermined distance from the upper stop position of the sample disc 5.

Moreover, after stopping the sample dispensing probe 16 in the upper stop position of the reaction disc 4, the controller 27 causes the sample dispensing probe 16 to move downward and, for example, to stop in the discharge position in which the end of the sample dispensing probe 16 contacts the bottom of the reaction cuvette 3.

Furthermore, the controller 27 causes the sample dispensing probe 16, which suctioned the sample in the first suctioning position, to stop in the first washing position, which is the first upper stop position of the washing unit 70.

Furthermore, after stopping the sample dispensing probe 16 that suctioned the sample in the second suctioning position in the second upper stop position, the controller 27 causes the sample dispensing probe 16 to move downward and to stop in the second washing position.

The data processing unit 30 shown in FIG. 1 is equipped with a calculating unit 31, which processes the standard data and the suspected data outputted from the photometry unit 13 of the analyzing unit 24, and generates the calibration data and the analytical data for each analysis item, and a data memory 32 that saves the standard data and the analytical data generated by the calculating unit 31.

The calculating unit 31 generates the calibration data showing a relationship between the standard value and the standard data for every analysis item based on the standard data output from the photometry unit 13 and the standard value set to the standard sample of the standard data, outputs the calibration data to the outputting unit 40, and saves the calibration data in the data memory 32.

Moreover, the calculating unit 31 reads the calibration data of the analysis item related to the suspected data output from the photometry unit 13 in the data memory 32.

The calculating unit 31 generates the analysis data expressed with a concentration value or an activity value using the calibration data read and the suspected data output from the photometry unit 13.

The calculating unit 31 outputs the generated analytical data to the outputting unit 40, and saves the data in the data memory 32.

The data memory 32 is equipped with memory devices, such as a hard disk, and stores the calibration data outputted from the calculating unit 31 for every analysis item. Moreover, the analytical data of each analysis item outputted from the calculating unit 31 are saved for every suspected sample.

The outputting unit 40 is equipped with a printing unit 41 to print out and display the calibration data and the analytical data outputted from the calculating unit 31 of the data processing unit 30.

Further, the printing unit 41 is equipped with a printer, etc. and prints the calibration data and the analytical data outputted from the calculating unit 31 to a printer sheet, etc. according to a format set up beforehand.

The display 42 is equipped with monitors, such as a CRT and a liquid crystal panel, and displays the calibration data and the analytical data that were outputted from the calculating unit 31.

Moreover, the display 42 displays an analysis parameter setting screen to set up the amount of samples and the amount of reagents discharged in the reaction cuvette 3 and the suctioning position where the sample dispensing probe suctions the sample in the sample container 17, and a reagent information setting screen for setting up the information on the reagent that is used for analysis of the analysis item set on the analysis parameter setting screen.

The operating unit 50 is equipped with input devices, such as a keyboard, a mouse, a button, and a touch key panel, and performs the input for setting up the analysis parameters for every analysis item, reagent information, etc.

The system controller 60 is equipped with a CPU and a memory circuit. After the system controller 60 memorizes the input information, such as the analysis parameters of each analysis item and the reagent information inputted by operation from the operating unit 50, in the memory circuit, based on these inputs, the system controller 60 initializes the analysis controller 25, the data processing unit 30, and the outputting unit 40, and controls the whole system.

Figure 3:
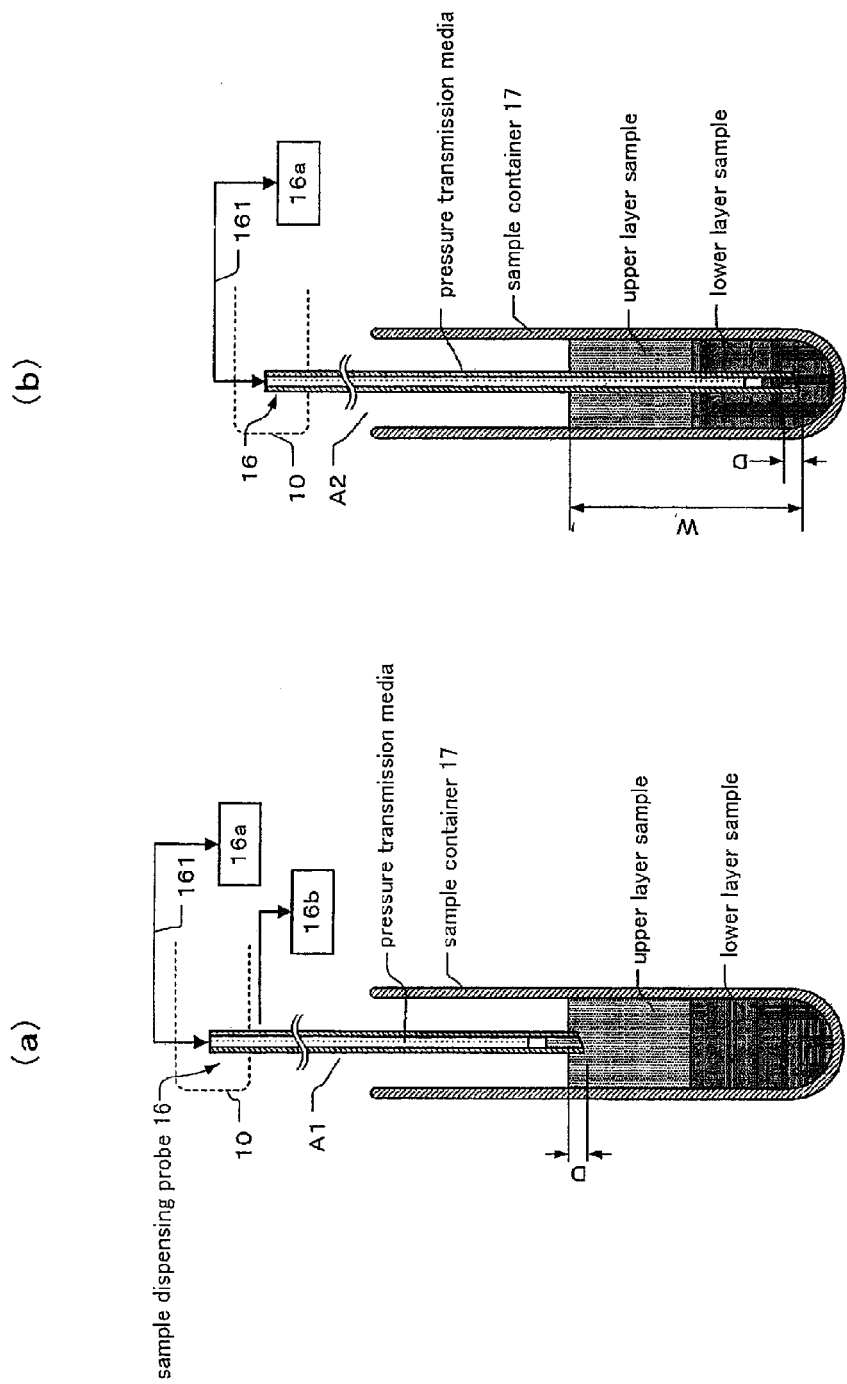
FIGS. 3a and 3b are sectional views showing the sample dispensing probe and the sample container stopped in the first and second suctioning positions in one embodiment.

Next, with reference to FIGS. 2 and 3, the composition of the sample dispensing probe 16 in the analyzing unit 24, and the first and second suctioning position are explained.

FIGS. 3a and 3b are sectional views showing the sample dispensing probe 16 and the sample container 17 stopped in the first and second suctioning positions.

FIG. 3a shows the sample dispensing probe 16 stopped in the first suctioning position, and FIG. 3b shows the sample dispensing probe 16 stopped in the second suction position.

The sample dispensing probe 16 has the shape of a tube that has an opening at both ends and performs suction and discharge of the sample at one end. Between the other end and a sample dispensing pump 16a is a flexible tube 161.

A pressure transfer media, such as pure water, fills the sample dispensing probe 16 and the tube 161.

Thereby, the pressure provided by the sample dispensing pump 16a suctioning and discharging operation is transmitted to the end part of the sample dispensing probe 16, and the sample dispensing probe 16 performs the suction and discharge operation from one end.

Moreover, one end of the sample dispensing probe 16 is held by the sample dispensing arm 10, and the sample dispensing probe 16 moves in a direction of the circumference by a rotating operation of the sample dispensing arm 10 and moves in the up-and-down direction by an up-and-down operation.

A blood collection tube of a predetermined size accommodates, for example, whole blood in the sample container 17.

Moreover, as shown in FIGS. 3a and 3b, the blood collection tube accommodates an upper layer sample of the serum and plasma positioned in the upper layer, and an up-and-down layer separation sample dividing the whole blood that includes the lower layer sample containing the blood cell component located in the lower layer into the up-and-down layer.

Furthermore, a sample cup and a test tube has a predetermined size to accommodate each sample, such as serum, plasma, and urine.

The controller 27 of the analysis controller 25 controls the mechanism of the mechanism part 26 that drives the sample dispensing arm 10 of the analyzing unit 24 based on the information on the suctioning position included in the analysis parameter supplied from the system controller 60.

Further, the controller 27 operates the sample dispensing arm 10 to make the sample dispensing probe 16 stop in each suctioning position.

As shown in FIG. 3a, the end part of the sample dispensing probe 16 moves a predetermined distance, for example about 2 mm, downwards from the surface of the sample in the sample container 17 and stops. The position at which the end part of the sample dispensing probe 16 stops is the first suctioning position A1 detected by the sample detecting unit 16b by contacting the sample in the sample container 17 with which the end part D of the sample dispensing probe 16 was held at the sample disc 5.

After the sample dispensing probe 16 stops in the first suctioning position A1, the controller 27 makes the sample dispensing probe 16 suction the serum or the plasma located in the upper layer according to the amount of samples set up in the sample dispensing probe 16 by controlling the mechanism of the mechanism part 26 that drives the sample dispensing pump 16a, based on the information on the amount of samples contained in the analysis parameter supplied from the system controller 60.

Thus, the sample can be suctioned in the sample dispensing probe 16 when stopped in the first suctioning position A1 for analysis of the analysis item, and it is not necessary to analyze the component contained in the sample positioned in the lower layer in the sample container 17.

Thus, unnecessary contact with external surfaces other than the end part D of the sample dispensing probe 16 that are not necessary to suction the sample, can be prevented, and a range of contamination by the sample with the external surface of the sample dispensing probe 16 can be reduced.

Moreover, as shown in FIG. 3b, the sample dispensing probe 16 is stopped in the second suctioning position A2 when the sample dispensing probe 16 moves from the upper stop position of the sample disc 5 a predetermined distance, and moves to a lower part rather than the first suctioning position A1.

After the sample dispensing probe 16 stops in the second suctioning position A2, the controller 27 makes the sample dispensing probe 16 suction the serum or the plasma located in the lower layer according to the amount of samples set up in the sample dispensing probe 16, by controlling the mechanism of the mechanism part 26 that drives the sample dispensing pump 16a based on the information on the amount of samples contained in the analysis parameter supplied from the system controller 60.

For example, when the analysis item is glycohemoglobin, the sample dispensing probe 16 is stopped in the second suctioning position A2 and the sample dispensing probe 16 can suction the whole blood.

In addition, when the sample dispensing probe 16 suctions the sample when the height of the probe in the sample container 17 is maximum in the second suctioning position A2, the external surface of a broad area W containing the end part D with the sample dispensing probe 16 is larger than the end part D of the sample dispensing probe 16 that will contact the sample.

Thus, in the analysis of the analysis item, when an analysis subject is the lower layer sample divided into the up-and-down layer of the sample container 17, and the whole blood, the sample dispensing probe 16 can be moved to the second suctioning position A2 where the lower layer sample can be suctioned.

Figure 4:
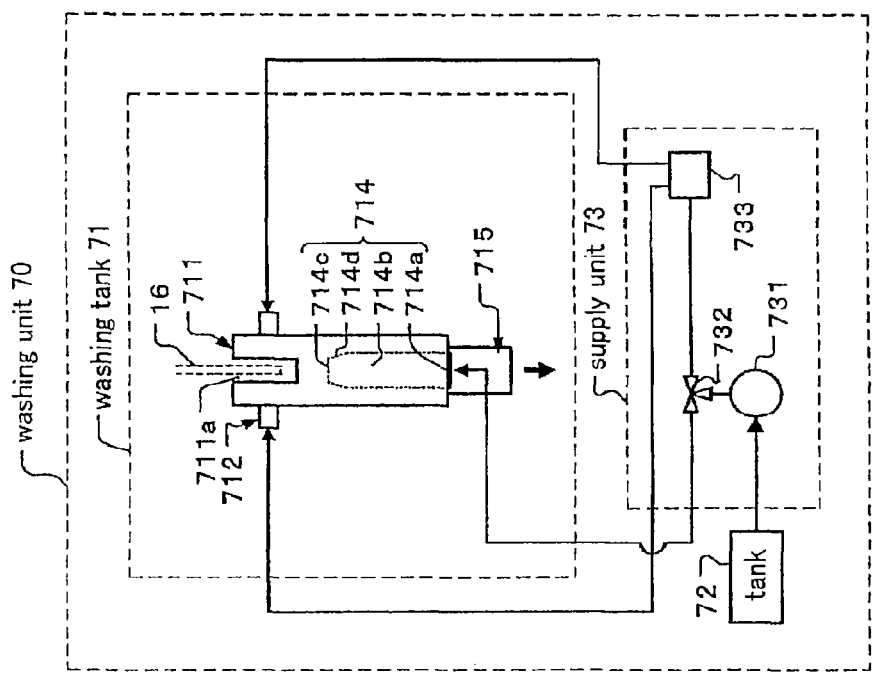
FIG. 4 is a figure showing an example of the composition of the washing unit in one embodiment.

Next, with reference to FIGS. 2-8, the composition of the washing unit 70 and the first and second washing position of the sample dispensing probe 16 are explained. FIG. 4 is a figure showing an example of the composition of the washing unit 70.

Figure 5:
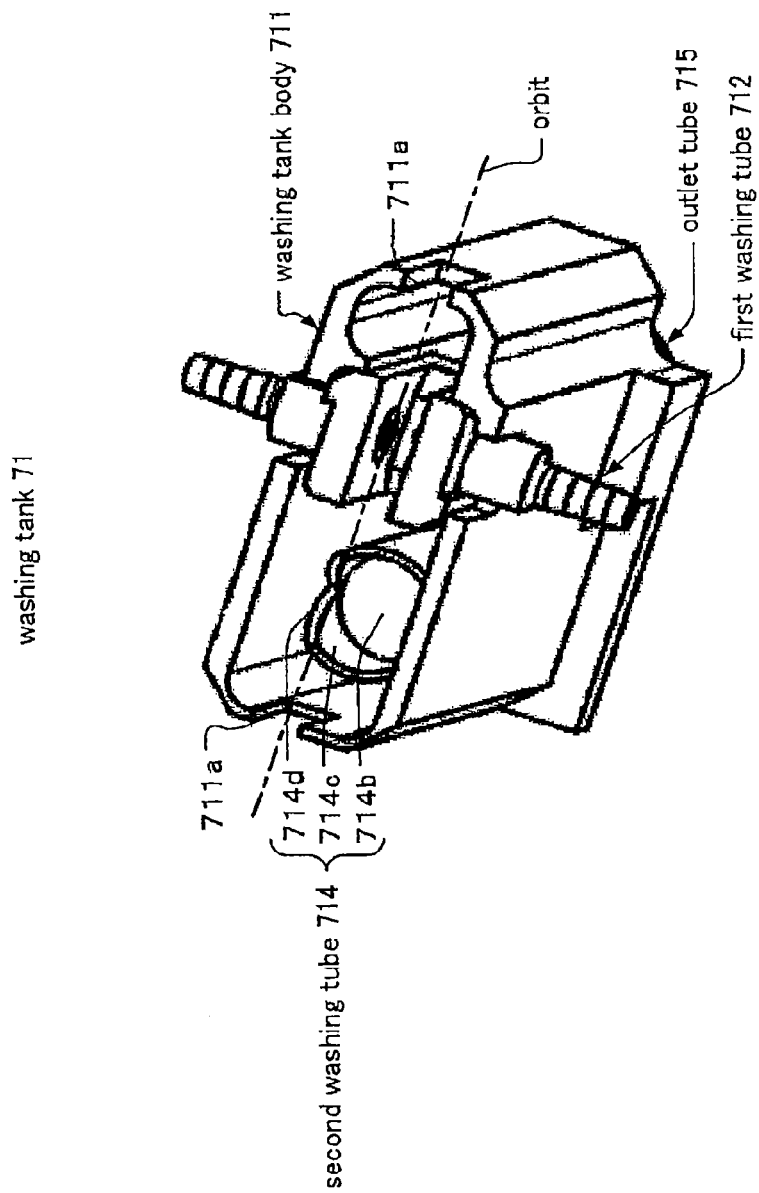
FIG. 5 is an outline view showing the composition of the washing tank in one embodiment.

Moreover, FIG. 5 is an outline view showing the composition of some washing parts of the washing unit 70.

Figure 6:
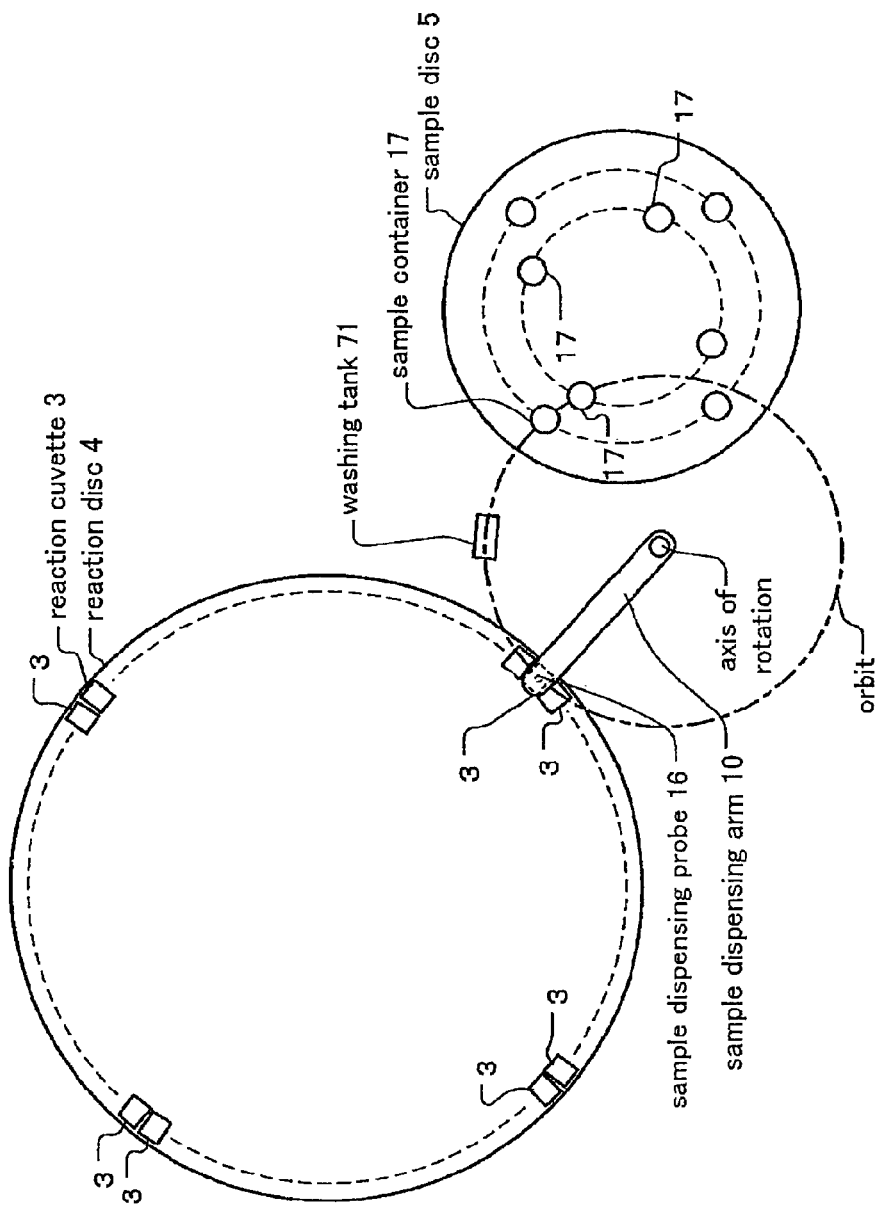
FIG. 6 is a figure showing an example of an arrangement of the washing tank in one embodiment.
Figure 7:
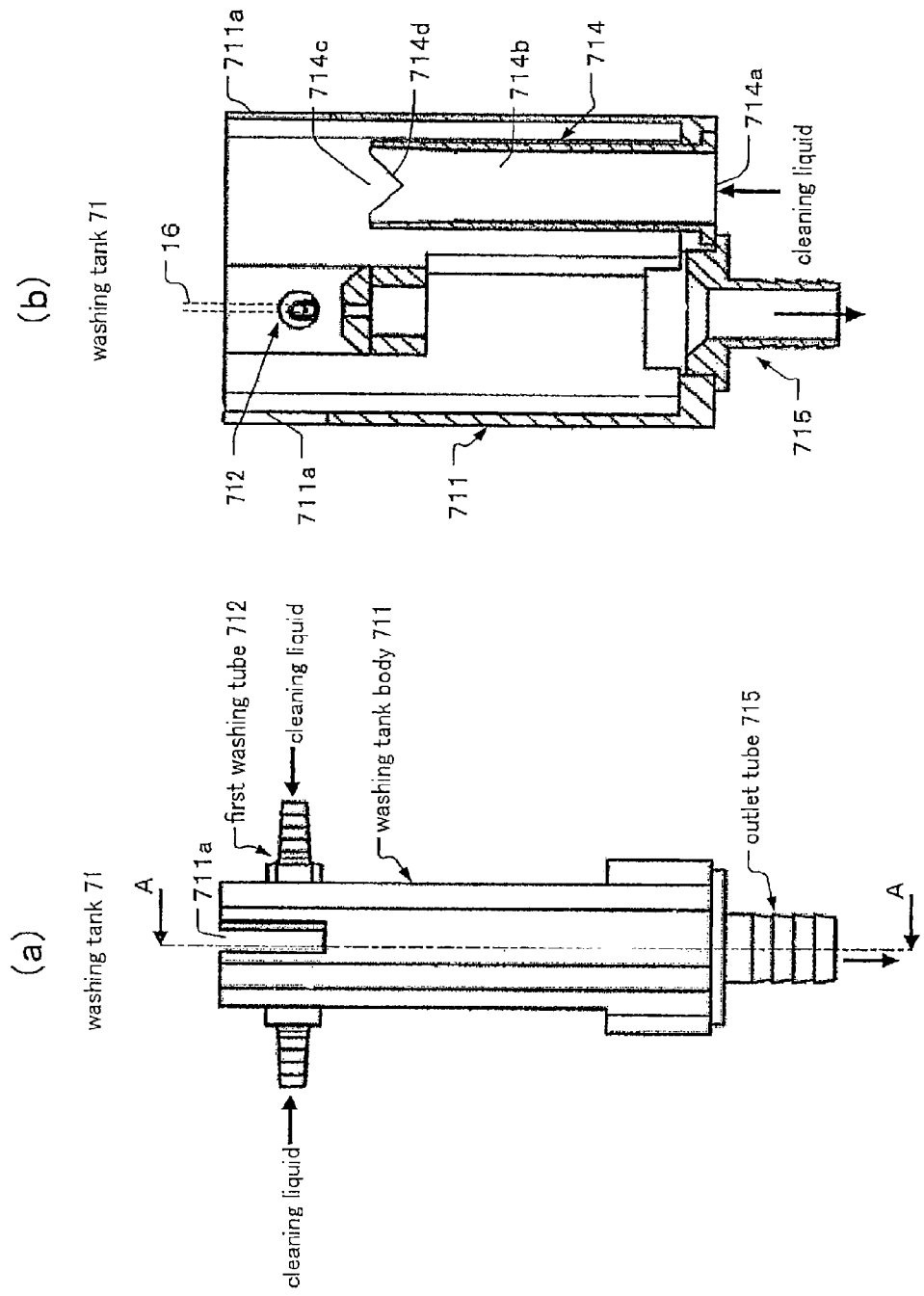
FIGS. 7a and 7b are figures showing details of the composition of the washing tank in one embodiment.
Figure 8:
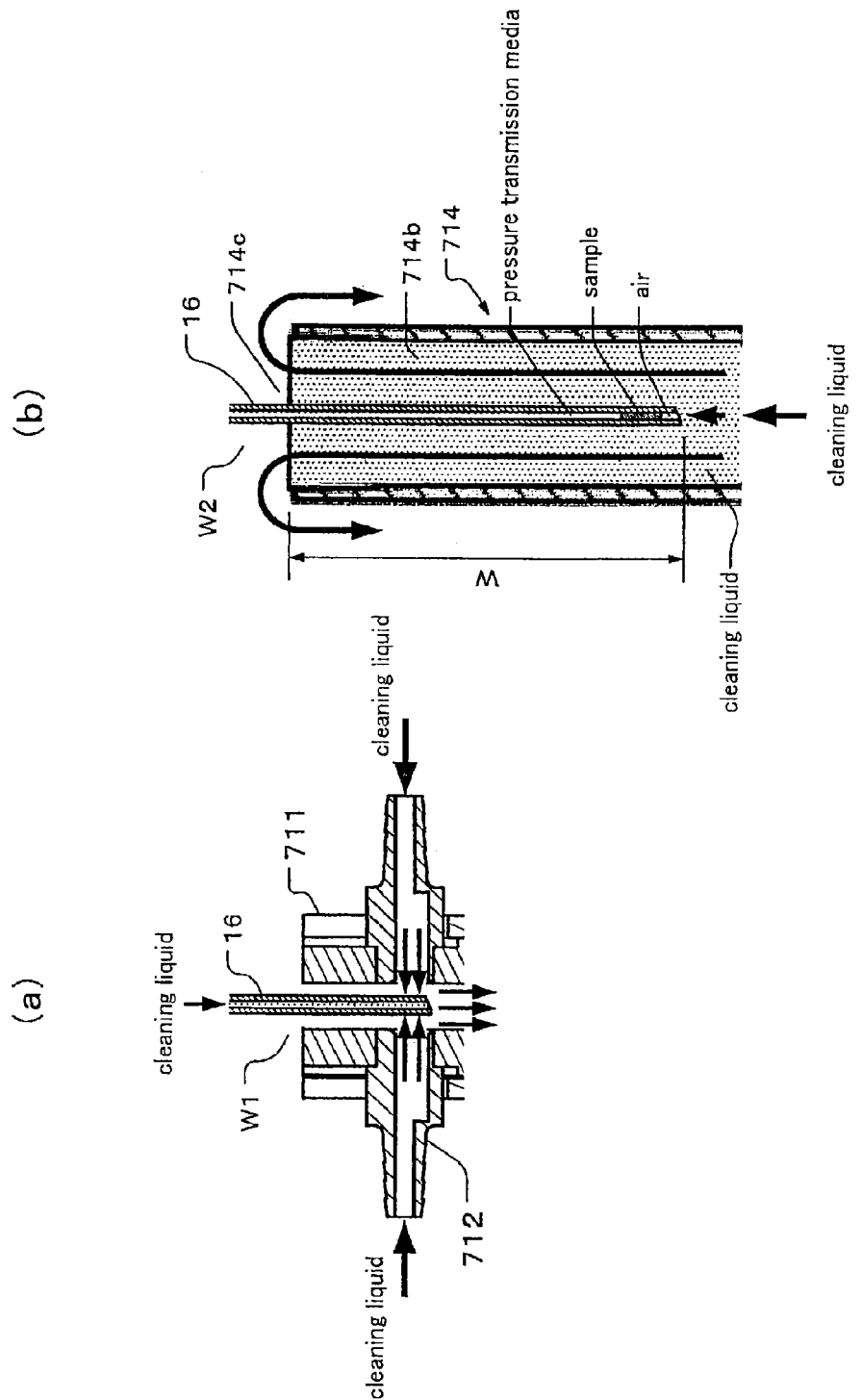
FIGS. 8a and 8b are sectional views showing the sample dispensing probe stopped in the first and second washing positions in one embodiment.
Figure 9:
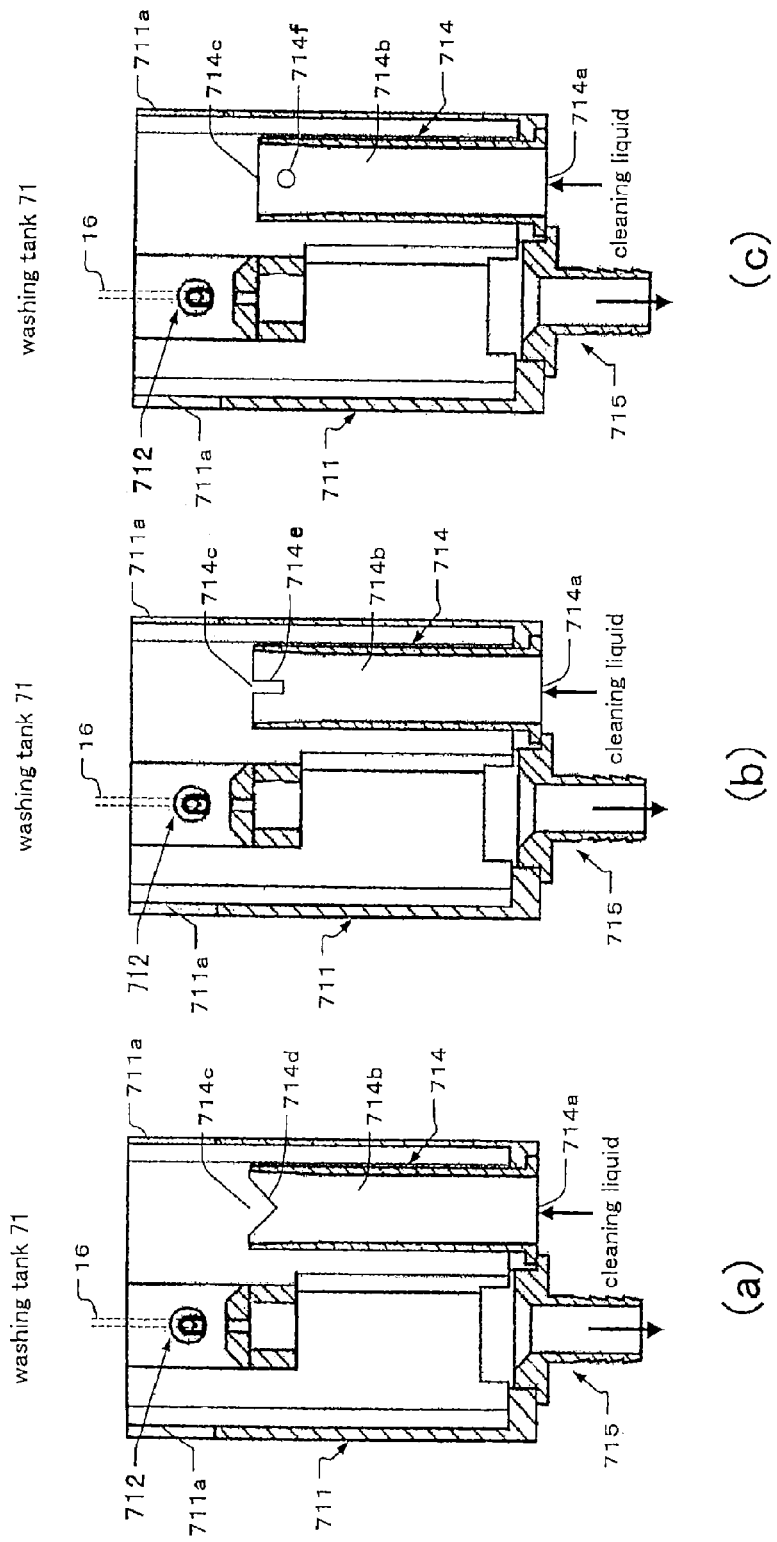
FIGS. 9a-9c are figures showing the inhibit unit that inhibits the force of the cleaning liquid flowing out from the second washing tube in the component of the washing tank in one embodiment.

Moreover, FIG. 6 is a figure showing an example of arrangement of the washing unit shown in FIG. 5.

Moreover, FIGS. 7a and 7b are figures showing the details of the composition of the washing unit shown in FIG. 5.

Moreover, FIGS. 8a and 8b are sectional views showing the sample dispensing probe 16 stopped in the first and second washing position of the washing unit 70.

In FIG. 4, the washing unit 70 includes a washing tank 71 that washes the sample dispensing probe 16, a tank 72 that stores the cleaning liquid for washing the sample dispensing probe 16, and a supply unit 73 that supplies the cleaning liquid stored by the tank 72. The washing unit 70 includes a first washing means that washes the external surface of the end part D of the sample dispensing probe that suctioned the sample in the sample container 17 in the first suctioning position A1 detected by sample detecting unit 16b and a second washing means that washes the broad area W on the external surface of the end part D of the sample dispensing probe 16 that suctioned the sample in the sample container 17 in the second suctioning position A2.

FIG. 5 is an outline view showing the composition of the washing tank 71.

As shown in FIG. 6, this washing tank 71 is arranged on the orbit of the circle shown with the dashed line of the sample dispensing probe 16 that moves between the upper stop position of the sample disc 5, and the upper stop position of the reaction disc 4, and includes a washing tank body 711, two first washing tubes 712, 713, which carry out discharge of the cleaning liquid to the end part D of the sample dispensing probe 16, a second washing tube 714, with which the broad area W portion of the sample dispensing probe 16 advances from the upper part, and an exhaust tube 715 that discharges cleaning liquid out of the washing tank body 711.

The washing tank body 711, the first washing tubes 712, 713, the exhaust tube 715, and the supply unit 73 function as a first washing means.

Moreover, the washing tank body 711, the second washing tube 714, the exhaust tube 715, and the supply unit 73 function as a second washing means.

FIGS. 7a and 7b are figures showing the details of the composition of the washing tank 71.

FIG. 7a is a side view of the washing tank 71, and FIG. 7b is an A-A sectional view of the washing tank 71 shown in FIG. 7a.

The washing tank body 711 of the washing tank 71 holds the first washing tubes 712, 713, the second washing tube, and an exhaust tube 715, and the washing tank body 711 leads the cleaning liquid used for washing of the sample dispensing probe 16 to the exhaust tube 715 to prevent the cleaning liquid from jumping out outside of the washing tank 71.

The upper end of the washing tank body 711 is positioned higher than the end part of the sample dispensing probe 16 when the sample dispensing probe 16 is at the top dead point.

For this reason, two notches 711a are prepared in both sides of the washing tank body 711 so that the sample dispensing probe 16, which moves in an orbit top, can be passed.

As shown in FIG. 8a, the first washing tubes 712, 713 are arranged on the washing tank body 711 face to face, and the sample dispensing probe 16 is stopped in the first washing position W1 where the end part D is inserted into the first washing tubes 712, 713.

The cleaning liquid supplied from the supply unit 73 and prepared in the washing tank body flows in a transverse direction from the discharge mouth turned to the external surface of the end part D of the sample dispensing probe 16, and the external surface of the end part D of the sample dispensing probe 16 is washed.

Moreover, cleaning liquid is supplied to the other ends of the sample dispensing probe 16 through the sample dispensing pump 16a and the tube 161 that are shown in FIGS. 3a and 3b.

The cleaning liquid that is passed through the inside of the sample dispensing probe 16 flows out from one end such that washing of the inside of the sample dispensing probe 16 is performed.

Thus, by making the cleaning liquid flow out from both sides towards the external surface of the end part D of the sample dispensing probe 16, the cleaning liquid can be made to cover the whole external surface of the end part D of the sample dispensing probe 16, and the whole external surface of the sample dispensing probe 16 that contacted the sample in the first suctioning position A1 can be washed powerfully in a short time.

Thereby, the sample adhering to the external surface of the sample dispensing probe 16 can be washed away.

Moreover, the sample adhering to the inside of the sample dispensing probe 16 can be washed out by supplying the cleaning liquid in the sample dispensing probe 16 from one end, and making it flow out from the other end.

The second washing tank 714 is arranged in the washing tank body 711 below the sample dispensing probe 16 that stopped in the second upper stop position of the washing unit 70, and is formed in order to make the cleaning liquid supplied from the supply unit 73 flow up.

The second washing tank 714 has an inlet port 714a that is located in the bottom of the washing tank body 711, a flow channel 714b that passes through vertically to make the cleaning liquid that flowed in from inlet port 714a flow up, and an exit 714c that is located in the superior extremity from which the cleaning liquid that flowed in the inside of the flow channel 714b flows out.

For example, two V-like dents 714d are prepared in a vertical direction to the orbit of the sample dispensing probe 16 of a superior-extremity side that forms the outlet port 714c as an inhibit unit to inhibit a force of the cleaning liquid that extends to the area of outlet port 714c and flows out from the outlet port 714c.

Moreover, the composition for inhibiting the force of the cleaning liquid that flows out from the outlet port 714c is not restricted to the dent 714d shown in FIG. 9a.

For example, as shown in FIG. 9b, two notches 714e having a form similar to notches 711a can be prepared in a vertical direction to the orbit of the sample dispensing probe 16 of the superior-extremity side that forms the outlet port 714c and, as shown in FIG. 9c, two holes 714f that connect the inside and outside of the washing tube can be prepared in a vertical direction to the orbit of the sample dispensing probe 16 of the superior-extremity side that forms the outlet port 714c.

Before the sample dispensing probe 16 moves downward from the second upper stop position, the cleaning liquid supplied further flows up inside of the flow channel 714b, and flows out of the outlet port 714c after the inside of flow channel 714b is filled with fresh cleaning liquid supplied from a supply unit 73.

The sample dispensing probe 16 moves downward from the upper part of the second washing tube 714 in the state where the cleaning liquid is flowing through, and as shown in FIG. 8b, it stops in the second washing position W2 where the portion of a broad area W is advanced into the second washing tube 714.

Since the end of the sample dispensing probe 16 begins to advance into the second washing tube 714, until just before moving upwards and starting the advance from the second washing tube 714, the cleaning liquid that flows through the inside of the second washing tube 714 washes the external surface of a broad area W of the sample dispensing probe 16.

The cleaning liquid that contains the sample that is exfoliated from the sample dispensing probe 16 by this washing flows out from the outlet port 714c.

Thus, by making the portion of the broad area W be in contact with the sample dispensing probe 16 advance into the second washing tube 714, which is flowing through upwards after the cleaning liquid has been filled by supply of the cleaning liquid from the supply unit 73, fresh cleaning liquid can go around to the whole external surface of the sample dispensing probe 16 that was in contact with the sample in the second suctioning position A2, and the cleaning liquid containing the sample is removed from the sample dispensing probe 16 and can be made to flow out of the second washing tube 714.

Thereby, the sample adhering to the external surface of the sample dispensing probe 16 can be washed away in a short time.

Moreover, this embodiment can prevent the cleaning liquid containing the sample from jumping out of the washing tank body 711 by inhibiting the force of the cleaning liquid that flows out from the outlet port 714c of the second washing tube 714.

Moreover, by preparing an inhibit unit, for example the dents 714d, the notches 714e, and the holes 714f, in the position that is in a vertical direction to the orbit of the sample dispensing probe 16, the force of the cleaning liquid containing the sample in the direction of notches 711a of the washing tank body 711 and in the direction of the first washing tubes 712, 713 is weakened, the cleaning liquid containing the sample is prevented from passing notches 711a and jumping out from the washing tank body 711, and the discharge mouth of the first washing tubes 712, 713 are prevented from being polluted with the cleaning liquid containing the sample.

An outlet tube 715 is formed in the inferior-extremity part of the washing tank body 711, and discharges the cleaning liquid that flowed out from the first washing tubes 712, 713, and the cleaning liquid that flowed out from the second washing tube 714 flows out of the washing tank body 711.

The supply unit 73 shown in FIG. 4 includes a pump 731 that suctions the cleaning liquid stored in the tank 72, and supplies the washing tank 71, a three-way electromagnetic valve 732 that is arranged between the pump 731 and the washing tank 71 and in which drive control is carried out by the controller 27 of the analysis controller 25, and a diverging tube 733 that is arranged between the three-way electromagnetic valve 732 and the washing tank 71 and branches the cleaning liquid from the three-way electromagnetic valve 732 and supplies to the first washing tubes 712, 713 of the washing tank 71.

While the three-way electromagnetic valve 732 opens between a pump 731 and the first washing tubes 712, 713, after closing between the pump 731 and the second washing tube 714, a pump 731 suctions the cleaning liquid in the tank 72, and supplies it to the first washing tubes 712, 713.

By this supply, the first washing tubes 712, 713 discharge cleaning liquid, and wash the external surface of the end part D of the sample dispensing probe 16 that stops in the first washing position W1.

Moreover, in washing of the sample dispensing probe 16 that stops in the second washing position W2, while the three-way electromagnetic valve 732 opens between a pump 731 and the second washing tube 714, after closing between a pump 731 and the first washing tubes 712, 713, the pump 731 suctions the cleaning liquid in the tank 72, and supplies it to the second washing tube 714.

By this supply, the external surface of the broad area W advanced into flow channel 714b is washed by the cleaning liquid flowing up inside of the flow channel 714b of the second washing tube 714.

In addition, the washing tank 71 can be divided into a first washing tank that is formed by the first washing tubes 712, 713 and a second washing tank that formed by the second washing tube 714, and the first and second washing tanks may have the outlet tube 715, respectively.

Figure 10:
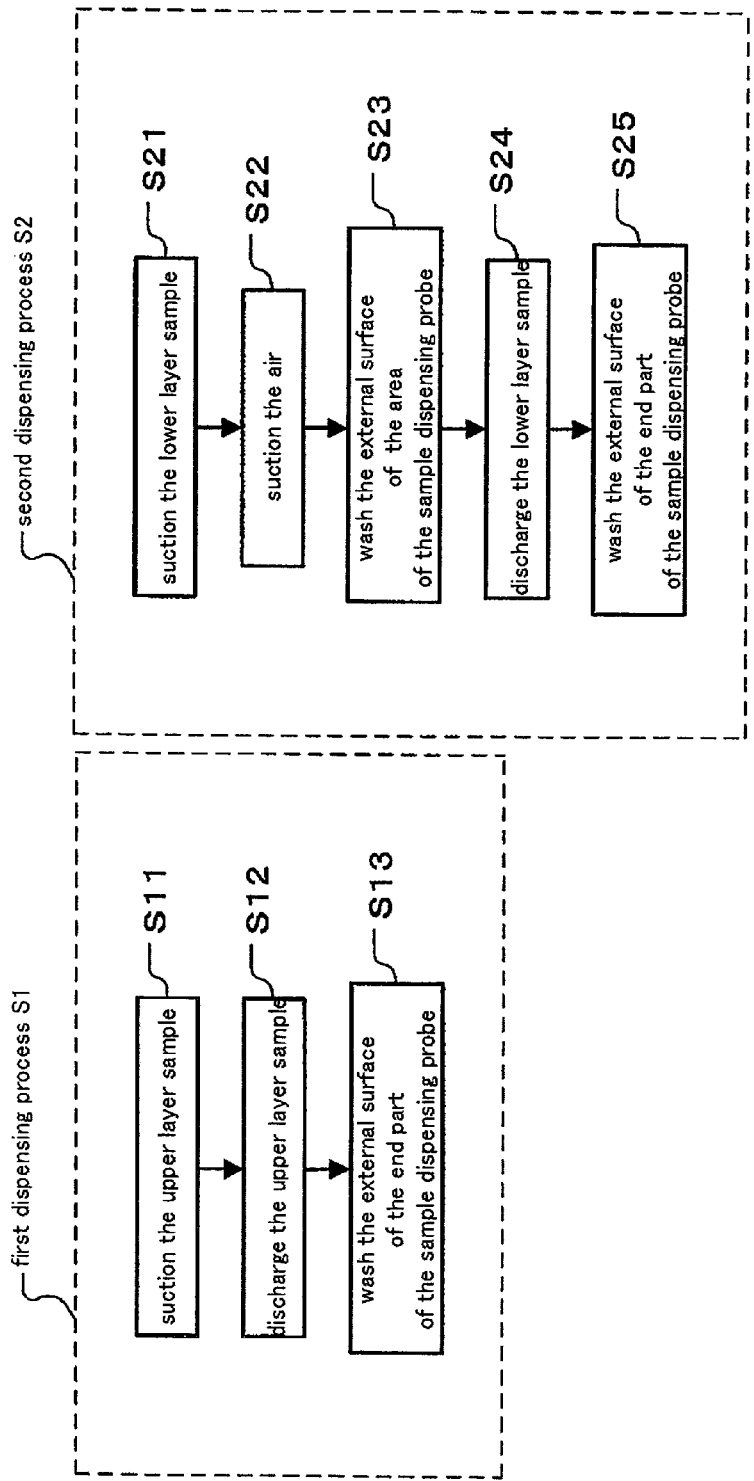
FIG. 10 is a flow chart showing the first and second dispensing processes in one embodiment.

Hereafter, with reference to FIGS. 1 and 10, the first dispensing process of the sample dispensing probe 16 that suctions the sample in the first suctioning position A1 and discharges in the discharge position, and a second dispensing process of the sample dispensing probe 16 that suctions the sample in the second suctioning position A2 and discharges in the discharge position are explained.

FIG. 10 is a flow chart that shows the first and second dispensing processes.

First, the first dispensing process S1 is explained.

The sample dispensing probe 16 moves from the first washing position W1 that is the home position to the upper stop position of the sample disc 5.

Air of a predetermined quantity is suctioned in parallel to this movement.

After stopping in the upper stop position of the sample disc 5, the probe moves downward and stops in the first suctioning position A1 where the upper sample in the sample container 17 is detected by the sample detecting unit 16b.

As shown in FIG. 3a, the upper layer sample in the sample container 17 is suctioned (Step S11).

After suctioning the upper layer sample in the sample container 17, the sample dispensing probe 16 moves upwards from the first suctioning position A1, and stops in the upper stop position of the sample disc 5.

After stopping in the upper stop position of the sample disc 5, the probe moves to the upper stop position of the reaction disc 4.

After stopping in the upper stop position of the reaction disc 4, the probe moves downward and stops in the discharge position.

The upper layer sample is discharged into the reaction cuvette 3 (Step S12).

After flowing out the sample into the reaction cuvette 3, the sample dispensing probe 16 moves upwards from the discharge position, and stops in the upper stop position of the reaction disc 4.

When dispensing additional similar samples after stopping in the upper stop position of the reaction disc 4, the probe moves from the upper stop position of the reaction disc 4 to the first suctioning position A1 or the second suctioning position A2.

Moreover, when finished dispensing the same sample, the probe moves from the upper stop position of the reaction disc 4, and stops in the first upper stop position of the washing unit 70 as the first washing position W1.

The inside of the sample dispensing probe 16 in contact with the sample is washed by the cleaning liquid supplied to the other end through the sample dispensing pump 16a and the tube 161 in the first washing position W1.

Moreover, the washing unit 70 washes the external surface of the end part D of the sample dispensing probe 16 in contact with the upper sample by the first washing tubes 712, 713 of the washing tank 71 discharging the cleaning liquid supplied from the supply unit 73 to the external surface of the end part D of the sample dispensing probe 16 from a transverse direction (Step S13).

Thus, washing can be performed without moving the sample dispensing probe 16 downward from the first upper stop position of the washing unit 70, the sample dispensing probe 16 is movable from the discharge position to the first washing position W1 in a short time.

Moreover, by making the cleaning liquid flow out from both sides towards the external surface of the end part D of the sample dispensing probe 16 in contact with the sample, the cleaning liquid can be made to cover the whole external surface in contact with the sample of the sample dispensing probe 16, and the sample adhering outside can be washed away in a short time.

Thereby, the contamination of the sample in the sample container 71 that is dispensed next can be prevented.

After being washed by the washing tank 71, the sample dispensing probe 16 stands by in preparation for dispensing a next sample in the first washing position W1.

Next, the second dispensing process S2 is explained.

The sample dispensing probe 16 moves from the first washing position W1 to the upper stop position of the sample disc 5.

A predetermined quantity of the air is suctioned in parallel to this movement.

After stopping in the upper stop position of the sample disc 5, the probe stops in the second suctioning position A2 that is under the sample a predetermined distance, rather than at the first suctioning position A1.

As shown in FIG. 3b, the lower layer sample in the sample container 17 is suctioned (Step S21).

After suctioning the lower layer sample in the sample container 17, the sample dispensing probe 16 moves upwards from the second suctioning position A2, and stops in the upper stop position of the sample disc 5.

After stopping in the upper stop position of the sample disc 5, the predetermined quantity of the air is suctioned (Step S22).

The sample dispensing probe 16 that suctioned the air moves from the upper stop position of the sample disc 5, and stops in the second upper stop position of the washing unit 70.

After stopping in the second upper stop position, the probe moves downward.

After the supply unit 73 of the washing unit 70 starts supply of the cleaning liquid to the second washing tube 714 and fills the inside of the second washing tube 714 with fresh cleaning liquid, before the sample dispensing probe 16 advances into the second washing tube 714, while the sample dispensing probe 16 advanced succeedingly and having stopped in the second washing position W2, continues supplying the cleaning liquid, the inside of the second washing tube 714 is made to flow up, and the external surface of the broad area W of the sample dispensing probe 16 is washed (Step S23).

Thus, before washing the external surface of the sample dispensing probe 16 that suctioned the lower layer sample, this embodiment can prevent cleaning liquid from mixing in the sample dispensing probe 16 at a time of outside washing, and diluting the sample by making the sample dispensing probe 16 suction the air adjoining the sample in the sample dispensing probe 16, and preparing the layer of air.

Moreover, by making the portion of the broad area W in contact with the sample of the sample dispensing probe 16 advance into the second washing tube 714, which is flowing through upwards after the cleaning liquid has been filled, fresh cleaning liquid can go around to the whole external surface of the sample dispensing probe 16 in contact with the sample, and the cleaning liquid containing the sample can be made to flow out of the second washing tube 714.

Thereby, the sample adhering to the external surface of the sample dispensing probe 16 can be washed in a short time, and this embodiment can prevent the sample adhering to the external surface of the sample dispensing probe 16 that is moving to the discharging position from jumping and polluting the circumference.

Moreover, this embodiment can prevent the sample unnecessary to analysis that is adhering to the sample dispensing probe 16 from falling into the reaction cuvette 3 from which the sample was obtained, and prevent the dispensing accuracy of the lower layer sample from falling.

Furthermore, the contamination of the sample in the sample container 17 that is dispensed next can be prevented.

The supply unit 73 stops supply of the cleaning liquid to the second washing tube 714 before the sample dispensing probe 16 that advances starts the advance from the second washing tube 714, and after the sample dispensing probe 16 leaves the second washing tube 714, the supply unit 73 supplies the cleaning liquid again, and fills the inside of the second washing tube 714 with fresh cleaning liquid.

Thus, before the sample dispensing probe 16 starts the advance from the second washing tube 714, this embodiment can prevent cleaning liquid which flowed out of the second washing tube 714 and adhered to an external surface of the sample dispensing probe 16 from falling in the reaction cuvette 3, and improve the dispensing accuracy of the lower layer sample by stopping supply of the cleaning liquid to the second washing tube 714.

After supply of the cleaning liquid, the sample dispensing probe 16 moves to the upper stop position of the reaction disc 4 and moves upwards slowly until all portions exit the second washing tube 714 filled with the cleaning liquid, and stops in the second upper stop position.

After stopping in the upper stop position, the probe moves downward and stops in a discharge position.

The probe discharges the lower layer sample into the reaction cuvette 3 (Step S24).

Thus, the cleaning liquid adhering to the external surface of the sample dispensing probe 16 can be removed with the surface tension of the cleaning liquid that accumulates in the upper part of the second washing tube 714 by moving the sample dispensing probe 16 upwards slowly from the second washing tube 714 filled with the cleaning liquid, after supply of the cleaning liquid is stopped.

Thereby, this embodiment can prevent the cleaning liquid from adhering to the external surface of the sample dispensing probe 16, and falling in the reaction cuvette 3 in which the sample is discharged, and prevent the dispensing accuracy of the lower layer sample from falling.

After flowing out the sample into the reaction cuvette 3, the sample dispensing probe 16 moves upwards from the discharge position, and stops in the upper stop position of the reaction disc 4.

When later performing dispensing of the same sample after stopping in the upper stop position of the reaction disc 4, the sample dispensing probe 16 moves to the first suctioning position A1 or the second suctioning position A2 from the upper stop position of the reaction disc 4.

Moreover, when finished dispensing the same sample, the probe moves from the upper stop position of the reaction disc 4, and stops in the first upper stop position of the washing unit 70 as the first washing position W1.

The inside in contact with the sample of the sample dispensing probe 16 is washed by the cleaning liquid supplied from one end through the sample dispensing pump 16a and the tube 161 in the first washing position W1.

Moreover, the washing unit 70 washes the external surface of the end part D of the sample dispensing probe 16 in contact with the upper sample by the first washing tubes 712, 713 of the washing tank 71 discharging the cleaning liquid supplied from the supply unit 73 to the external surface of the end part D of the sample dispensing probe 16 from a transverse direction (Step S25).

Thus, by making the cleaning liquid flow out from both sides towards the external surface of the end part D of the sample dispensing probe 16, when the sample flows out, the sample adhering to the end of the sample dispensing probe 16 can be washed away.

Thereby, the contamination of the sample in the sample container 71 that is dispensed next can be prevented.

After being washed by the washing tank 71, the sample dispensing probe 16 stands by in preparation for the next dispensing in the first washing position W1.

According to one embodiment described above, the two first washing tubes 712, 713 are arranged on the washing tank body 711 face to face, and the sample dispensing probe 16 is stopped in the first washing position W1 where the end part D is inserted into the first washing tubes 712, 713.

By making the cleaning liquid supplied from the supply unit 73 flow out from the first washing tubes 712, 713, the cleaning liquid can be made to cover the whole external surface of the sample dispensing probe 16 in contact with the sample in the first suctioning position A1, and the sample adhering outside can be washed away in a short time.

Thereby, the contamination of the sample in the sample container 17 that is dispensed next can be prevented.

Moreover, the second washing tube 714 is arranged in the washing tank body 711, and the sample dispensing probe 16 is moved downward from the upper part of the second washing tube 714.

By making the portion of the broad area W in contact with the sample of the sample dispensing probe 16 advance into the second washing tube 714, which is flowing through upwards after the cleaning liquid has been filled by the cleaning liquid from the supply unit 73, fresh cleaning liquid can go around to the whole external surface of the sample dispensing probe 16 in contact with the sample in the second suctioning position A2, and the cleaning liquid containing the sample can be made to flow out of the second washing tube 714.

Thereby, the sample adhering to the external surface of the sample dispensing probe 16 can be washed in a short time, and this embodiment can prevent the sample adhering the external surface of the sample dispensing probe 16 that is moving to the discharging position from jumping and polluting the circumference.

Moreover, this embodiment prevents the sample that is not necessary for analysis, but is adhering to the sample dispensing probe 16 from falling in the reaction cuvette 3 with which the sample flowed out, and prevents the dispensing accuracy of a lower layer sample from falling.

Furthermore, the contamination of the sample in the sample container 17 that is dispensed next can be prevented.

Furthermore, the sample adhering to the external surface of the sample dispensing probe 16 can be removed by moving the sample dispensing probe 16 upwards slowly after stopping supply of the cleaning liquid to the second washing tube 714 until all the portions of the sample dispensing probe 16 exit the second washing tube 714, where cleaning liquid is filled.

Thereby, this embodiment can prevent the cleaning liquid from adhering to the external surface of the sample dispensing probe 16, and falling into the reaction cuvette 3 in which the sample is discharged, and can prevent the dispensing accuracy of the lower layer sample from falling.

Thus, the external surface of the sample dispensing probe in contact with the sample can be washed, without reducing the dispensing accuracy of a lower layer sample.

What is claimed is:

1. An automatic analyzer that dispenses a sample and a reagent in a reaction cuvette and measures a mixed solution, comprising:
    a dispensing probe configured to suction the sample from a sample container, to move in an orbit between the sample container and the reaction cuvette, and to discharge the sample into the reaction cuvette;
    a detecting unit configured to detect the sample in the sample container by an end part of the dispensing probe contacting the sample; and
    a washer configured to wash an external surface of the dispensing probe, wherein said washer includes a washing tank body including notches through which the dispensing probe is passed, a first washing tube, a second washing tube, and an inlet port configured to supply cleaning liquid in the second washing tube, the inlet port being located in a bottom part of the second washing tube, wherein the dispensing probe enters into an upper part of the second washing tube, and a pump that supplies the second washing tube with the cleaning liquid,
    the first washing tube is supported by the washing tank body and configured to eject the cleaning liquid toward the external surface of the dispensing probe that is moving in the orbit to wash the external surface, and
    the second washing tube is supported by and arranged within the washing tank body and being erected thereon, and located alongside of the first washing tube on the orbit, and is configured to have the dispensing probe enter into an upper part thereof to wash the external surface of the dispensing probe, and
    the second washing tube includes an inhibitor that is either a hole, dent, or notch formed at a superior extremity side that forms an outlet port of the second washing tube and located in a position in a direction perpendicular to an orbit direction of the orbit, the direction being a direction in which the second washing tube is arranged in the washing tank body, and the inhibitor is structurally configured to inhibit a force of the cleaning liquid that flows out from the superior extremity of the second washing tube to prevent the cleaning liquid containing the sample from passing the notches and escaping from the washing tank body.

2. The automatic analyzer according to claim 1, further comprising a controller configured to cause the pump to cause the cleaning liquid to flow up through an inside of the second washing tube.

3. The automatic analyzer according to claim 2, wherein the controller is further configured to cause the pump to start supplying the cleaning liquid before the dispensing probe enters into the second washing tube and stop supplying the cleaning liquid before the dispensing probe starts exiting from the second washing tube.

4. The automatic analyzer according to claim 1, further comprising a controller configured to cause the washer to wash the dispensing probe that has suctioned the sample from the sample container before discharging the sample into the reaction cuvette.

5. The automatic analyzer according to claim 4, wherein the controller is further configured to cause the dispensing probe to suction air after suctioning the sample in the sample container before entering into the second washing tube.

6. The automatic analyzer according to claim 1, further comprising a controller configured to cause the dispensing probe to suction air after suctioning the sample in the sample container before entering into the second washing tube.

7. The automatic analyzer according to claim 1, wherein the inhibitor is a hole that is prepared in a predetermined position that is perpendicularly set to the orbit of the dispensing probe in a sidewall of the second washing tube and to connect an inside and an exterior of the second washing tube.

8. The automatic analyzer according to claim 1, wherein the inhibitor is a dent that is prepared in a predetermined position that is perpendicularly set to the orbit of the dispensing probe in a sidewall of the second washing tube.

9. The automatic analyzer according to claim 1, wherein the detector unit is configured to detect a first suction position by contact between an end part of the dispensing probe and the sample, a second suction position is located on a lower side of the first suction position, and the sample suctioned by the dispensing probe in the second suction position is a lower layer sample containing blood cells divided into an upper layer and a lower layer from whole blood.

10. The automatic analyzer according to claim 9, further comprising a controller configured to control the pump to supply the cleaning liquid to cause the first washing tube to eject the cleaning liquid from two or more directions toward an outside of the end part of the dispensing probe that has suctioned the sample in the sample container at the first suction position.

* * * * *